US007049422B2

(12) United States Patent
Deen et al.

(10) Patent No.: US 7,049,422 B2
(45) Date of Patent: May 23, 2006

(54) TUMOR NECROSIS RELATED RECEPTOR, TR7

(75) Inventors: Keith Charles Deen, Glenmoore, PA (US); Mark R. Hurle, Norristown, PA (US); Peter Young, Lawrenceville, NJ (US); Kong B. Tan, Philadelphia, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/663,157

(22) Filed: Sep. 15, 2003

(65) Prior Publication Data

US 2004/0132057 A1 Jul. 8, 2004

Related U.S. Application Data

(62) Division of application No. 09/314,844, filed on May 19, 1999, now Pat. No. 6,660,839, which is a division of application No. 08/959,382, filed on Oct. 28, 1997, now Pat. No. 6,013,476.

(60) Provisional application No. 60/041,796, filed on Apr. 2, 1997.

(51) Int. Cl.

| | |
|---|---|
| ***C12N 15/00*** | (2006.01) |
| ***C12N 15/85*** | (2006.01) |
| ***C07H 21/04*** | (2006.01) |
| ***C07K 119/00*** | (2006.01) |

(52) U.S. Cl. .................. 536/23.2; 435/69.1; 435/320.1; 435/325; 435/252.3; 536/23.1; 536/23.5; 530/350

(58) Field of Classification Search ................ 435/69.1, 435/320.1, 325, 252.3; 536/23.2, 23.5, 23.1; 530/350

See application file for complete search history.

(56) References Cited

U.S. PATENT DOCUMENTS

| | | | | |
|---|---|---|---|---|
| 5,350,836 A | | 9/1994 | Kopchick et al. | |
| 6,358,508 B1 | | 3/2002 | Ni et al. | |
| 6,660,839 B1 | * | 12/2003 | Deen et al. | 530/350 |
| 2002/0164684 A1 | | 11/2002 | Ni et al. | |
| 2002/0168359 A1 | | 11/2002 | Ni et al. | |

FOREIGN PATENT DOCUMENTS

| | | |
|---|---|---|
| WO | WO 96/43095 | 10/1996 |

OTHER PUBLICATIONS

Schmidt, et al, 2003, J. Exp. Med., 197(1): 51–62.*
Curfs, et al, 1997, Clin. Microbiol. Rev., 10(4): 742–780.*
Murdoch and Finn, 2000, Blood, 15(95): 3032–3043.*
Allende, et al, 2001, Clin. Diagn. Lab. Immunol., 8(1): 133–137.*
Bork, P. (1996), Go hunting in sequence database but watch out for the tarps. Trends Genetics, 12(10):425–427.
Pilbeam, et al. 1993, Bone. 14:717–720.
Bork, P. (1998), Powers and Pitfalls in Sequence Analysis: The 70% Hurdle, Genome Res., 10:398–400, esp. p. 400.
Doerks, T. (1998), Protein annotation: detective work for function prediction. Trends Genetics. 14(6):248–250.
Kwon et al., “A newly–identified member of the tumor necrosis factor receptor superfamily”, Journal of Allergy and Clinical Immunology, vol. 99 (1), pp. 5467 (1997). ABSTACT.
Accession # AA351536, Adams, 1997.
Accession # AA155873, Hillrer, 1996.
Accession # D59902, Fujiwara, 1995.
Accession # AA357321 Adams, 1997.
Accession # AA374471 Adams, 1995.
Accession # N49208 Hillrer, 1996.
Accession # H44577 Hillrer, 1995.
EST #2051015.
STN Search Print out of TNF–Receptor Related Products.
Skolnick, J. (2000), From genes to protein structure and function: novel applications of computational approaches in the genomic era., Trends in Biotech., 18(1):34–39, esp. p. 36.
Murdoch, et al. (2000) Blood, 95(10):3032–3043.
Vukicevic, S. et al., (1996) Induction of nephrogenic mesenchyme by osteogenic protein 1 (bone morphogenetic protein 7) PNAS USA 93–9021–9026.
Massague, J. (1987) The TGF–B Family of Growth and Differentiation Factors. Cell 49:437–438.
Smith, T. et al., (1997) The challenges of genome sequence annotation or “The devil is in the details”, Nature Biotech. 15:1222–1223.
Brenner, S. (1999) Errors in genome annotation. Trends in Genetics 15(4):132–133.
Frommel et al., J. Mol, Eval 198, p, 233–57, vol. 21.
Bowie et al., *Science 247*, 1990, p 1306.
Ngo et al., The Protein Folding Problem, Ed Mertz, 1994, p. 4337.
George et al. et al. Macro mol., Seq & Syn, 1988, p. 127–149.

(Continued)

*Primary Examiner*—Elizabeth Kemmerer
*Assistant Examiner*—Sandra Wegert
(74) *Attorney, Agent, or Firm*—RatnerPrestia

(57) ABSTRACT

TR7 polypeptides and polynucleotides and methods for producing such polypeptides by recombinant techniques are disclosed. Also disclosed are methods for utilizing TR7 polypeptides and polynucleotides in the design of protocols for the treatment of chronic and acute inflammation, arthritis, septicemia, autoimmune diseases (such as inflammatory bowel disease and psoriasis), transplant rejection, graft versus host disease, infection, stroke, ischemia, acute respiratory disease syndrome, restenosis, brain injury, AIDS, bone diseases, cancer (such as lymphoproliferative disorders), atherosclerosis, and Alzheimers disease, among others and diagnostic assays for such conditions.

17 Claims, No Drawings

OTHER PUBLICATIONS

ACCESSION # H44234.

ACCESSION # AA382042.

EST # 1502886.

EST # 843791.

Fujiwara et al., "Unpublished" Database EMBL, XP002072603, Entryname HS073E08B, Aug. 27, 1995. Abstract.

Copy of European Search Report.

Bork, P. (2000) Powers and Pitfalls in Sequence Analysis: The 70% Hurdle. Genome Research 10:398–400.

* cited by examiner

SEQUENCE LISTING

<160> NUMBER OF SEQ ID NOS: 6

<210> SEQ ID NO 1
<211> LENGTH: 2186
<212> TYPE: DNA
<213> ORGANISM: HOMO SAPIENS

<400> SEQUENCE: 1

```
tcagccatgg ggacctctcc gagcagcagc accgccctcg cctcctgcag ccgcatcgcc     60
cgccgagcca cagccacgat gatcgcgggc tcccttctcc tgcttggatt ccttagcacc    120
accacagctc agccagaaca gaaggcctcg aatctcattg gcacataccg ccatgttgac    180
cgtgccaccg gccaggtgct aacctgtgac aagtgtccag caggaaccta tgtctctgag    240
cattgtacca acacaagcct gcgcgtctgc agcagttgcc ctgtggggac ctttaccagg    300
catgagaatg gcatagagaa atgccatgac tgtagtcagc catgcccatg gccaatgatt    360
gagaaattac cttgtgctgc cttgactgac cgagaatgca cttgcccacc tggcatgttc    420
cagtctaacg ctacctgtgc cccccatacg gtgtgtcctg tgggttgggg tgtgcggaag    480
aaagggacag agactgagga tgtgcggtgt aagcagtgtg ctcggggtac cttctcagat    540
gtgccttcta gtgtgatgaa atgcaaagca tacacagact gtctgagtca gaacctggtg    600
gtgatcaagc cggggaccaa ggagacagac aacgtctgtg gcacactccc gtccttctcc    660
agctccacct caccttcccc tggcacagcc atctttccac gccctgagca catggaaacc    720
catgaagtcc cttcctccac ttatgttccc aaaggcatga actcaacaga atccaactct    780
tctgcctctg ttagaccaaa ggtactgagt agcatccagg aagggacagt ccctgacaac    840
acaagctcag caaggggggaa ggaagacgtg aacaagaccc tcccaaacct tcaggtagtc    900
aaccaccagc aaggccccca ccacagacac atcctgaagc tgctgccgtc catggaggcc    960
actgggggcg agaagtccag cacgcccatc aagggcccca agaggggaca tcctagacag   1020
aacctacaca agcattttga catcaatgag catttgccct ggatgattgt gcttttcctg   1080
ctgctggtgc ttgtggtgat tgtggtgtgc agtatccgga aaagctcgag gactctgaaa   1140
aaggggcccc ggcaggatcc cagtgccatt gtggaaaagg cagggctgaa gaaatccatg   1200
actccaaccc agaaccggga gaaatggatc tactactgca atggccatgg tatcgatatc   1260
ctgaagcttg tagcagccca agtgggaagc cagtggaaag atatctatca gtttctttgc   1320
aatgccagtg agagggaggt tgctgctttc tccaatgggt acacagccga ccacgagcgg   1380
gcctacgcag ctctgcagca ctggaccatc cggggccccg aggccagcct cgcccagcta   1440
attagcgccc tgcgccagca ccggagaaac gatgttgtgg agaagattcg tgggctgatg   1500
gaagacacca cccagctgga aactgacaaa ctagctctcc cgatgagccc cagcccgctt   1560
agcccgagcc ccatccccag ccccaacgcg aaacttgaga attccgctct cctgacggtg   1620
gagccttccc cacaggacaa gaacaagggc ttcttcgtgg atgagtcgga gccccttctc   1680
cgctgtgact ctacatccag cggctcctcc gcgctgagca ggaacggttc ctttattacc   1740
aaagaaaaga aggacacagt gttgcggcag gtacgcctgg acccctgtga cttgcagcct   1800
atctttgatg acatgctcca ctttctaaat cctgaggagc tgcgggtgat tgaagagatt   1860
ccccaggctg aggacaaact agaccggcta ttcgaaatta ttggagtcaa gagccaggaa   1920
gccagccaga ccctcctgga ctctgtttat agccatcttc ctgacctgct gtagaacata   1980
gggatactgc attctggaaa ttactcaatt tagtggcagg gtggtttttt aattttcttc   2040
```

-continued

```
tgtttctgat ttttgttgtt tggggtgtgt gtgtgtgttt gtgtgtgtgt gtgtgtgtgt   2100

gtgtgtgtgt gtttaacaga gaaaatgggc agtgcttgaa ttctttctcc ttctctctct   2160

ctcttttttt tttaaataac tcctct                                         2186


<210> SEQ ID NO 2
<211> LENGTH: 655
<212> TYPE: PRT
<213> ORGANISM: HOMO SAPIENS

<400> SEQUENCE: 2

Met Gly Thr Ser Pro Ser Ser Ser Thr Ala Leu Ala Ser Cys Ser Arg
1               5                   10                  15

Ile Ala Arg Arg Ala Thr Ala Thr Met Ile Ala Gly Ser Leu Leu Leu
            20                  25                  30

Leu Gly Phe Leu Ser Thr Thr Thr Ala Gln Pro Glu Gln Lys Ala Ser
        35                  40                  45

Asn Leu Ile Gly Thr Tyr Arg His Val Asp Arg Ala Thr Gly Gln Val
    50                  55                  60

Leu Thr Cys Asp Lys Cys Pro Ala Gly Thr Tyr Val Ser Glu His Cys
65                  70                  75                  80

Thr Asn Thr Ser Leu Arg Val Cys Ser Ser Cys Pro Val Gly Thr Phe
                85                  90                  95

Thr Arg His Glu Asn Gly Ile Glu Lys Cys His Asp Cys Ser Gln Pro
            100                 105                 110

Cys Pro Trp Pro Met Ile Glu Lys Leu Pro Cys Ala Ala Leu Thr Asp
        115                 120                 125

Arg Glu Cys Thr Cys Pro Pro Gly Met Phe Gln Ser Asn Ala Thr Cys
    130                 135                 140

Ala Pro His Thr Val Cys Pro Val Gly Trp Gly Val Arg Lys Lys Gly
145                 150                 155                 160

Thr Glu Thr Glu Asp Val Arg Cys Lys Gln Cys Ala Arg Gly Thr Phe
                165                 170                 175

Ser Asp Val Pro Ser Ser Val Met Lys Cys Lys Ala Tyr Thr Asp Cys
            180                 185                 190

Leu Ser Gln Asn Leu Val Val Ile Lys Pro Gly Thr Lys Glu Thr Asp
        195                 200                 205

Asn Val Cys Gly Thr Leu Pro Ser Phe Ser Ser Ser Thr Ser Pro Ser
    210                 215                 220

Pro Gly Thr Ala Ile Phe Pro Arg Pro Glu His Met Glu Thr His Glu
225                 230                 235                 240

Val Pro Ser Ser Thr Tyr Val Pro Lys Gly Met Asn Ser Thr Glu Ser
                245                 250                 255

Asn Ser Ser Ala Ser Val Arg Pro Lys Val Leu Ser Ser Ile Gln Glu
            260                 265                 270

Gly Thr Val Pro Asp Asn Thr Ser Ser Ala Arg Gly Lys Glu Asp Val
        275                 280                 285

Asn Lys Thr Leu Pro Asn Leu Gln Val Val Asn His Gln Gln Gly Pro
    290                 295                 300

His His Arg His Ile Leu Lys Leu Leu Pro Ser Met Glu Ala Thr Gly
305                 310                 315                 320

Gly Glu Lys Ser Ser Thr Pro Ile Lys Gly Pro Lys Arg Gly His Pro
                325                 330                 335

Arg Gln Asn Leu His Lys His Phe Asp Ile Asn Glu His Leu Pro Trp
```

-continued

```
            340                 345                 350

Met Ile Val Leu Phe Leu Leu Leu Val Leu Val Val Ile Val Val Cys
        355                 360                 365

Ser Ile Arg Lys Ser Ser Arg Thr Leu Lys Lys Gly Pro Arg Gln Asp
    370                 375                 380

Pro Ser Ala Ile Val Glu Lys Ala Gly Leu Lys Lys Ser Met Thr Pro
385                 390                 395                 400

Thr Gln Asn Arg Glu Lys Trp Ile Tyr Tyr Cys Asn Gly His Gly Ile
                405                 410                 415

Asp Ile Leu Lys Leu Val Ala Ala Gln Val Gly Ser Gln Trp Lys Asp
            420                 425                 430

Ile Tyr Gln Phe Leu Cys Asn Ala Ser Glu Arg Glu Val Ala Ala Phe
        435                 440                 445

Ser Asn Gly Tyr Thr Ala Asp His Glu Arg Ala Tyr Ala Ala Leu Gln
    450                 455                 460

His Trp Thr Ile Arg Gly Pro Glu Ala Ser Leu Ala Gln Leu Ile Ser
465                 470                 475                 480

Ala Leu Arg Gln His Arg Arg Asn Asp Val Val Glu Lys Ile Arg Gly
                485                 490                 495

Leu Met Glu Asp Thr Thr Gln Leu Glu Thr Asp Lys Leu Ala Leu Pro
            500                 505                 510

Met Ser Pro Ser Pro Leu Ser Pro Ser Pro Ile Pro Ser Pro Asn Ala
        515                 520                 525

Lys Leu Glu Asn Ser Ala Leu Leu Thr Val Glu Pro Ser Pro Gln Asp
    530                 535                 540

Lys Asn Lys Gly Phe Phe Val Asp Glu Ser Glu Pro Leu Leu Arg Cys
545                 550                 555                 560

Asp Ser Thr Ser Ser Gly Ser Ser Ala Leu Ser Arg Asn Gly Ser Phe
                565                 570                 575

Ile Thr Lys Glu Lys Lys Asp Thr Val Leu Arg Gln Val Arg Leu Asp
            580                 585                 590

Pro Cys Asp Leu Gln Pro Ile Phe Asp Asp Met Leu His Phe Leu Asn
        595                 600                 605

Pro Glu Glu Leu Arg Val Ile Glu Glu Ile Pro Gln Ala Glu Asp Lys
    610                 615                 620

Leu Asp Arg Leu Phe Glu Ile Ile Gly Val Lys Ser Gln Glu Ala Ser
625                 630                 635                 640

Gln Thr Leu Leu Asp Ser Val Tyr Ser His Leu Pro Asp Leu Leu
                645                 650                 655


<210> SEQ ID NO 3
<211> LENGTH: 584
<212> TYPE: DNA
<213> ORGANISM: HOMO SAPIENS
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (15)..(15)
```

<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t

<400> SEQUENCE: 3

```
gcgnccgcgn ngngngcaag gtgctgagcg ccccctagngc ctcccttgcc gcctccctcc     60

tctgcccggc cgtagcagtg cacatggggt gttggaggta gatgggctcc cggccgggag    120

gcggcggtgg atgcggcgct gggcagaagc agccgccgat tccagctgcc ccgcgcgccc    180

cggccacctt gcgagtcccc ggttcagcca tggggacctc tccgagcagc agcaccgccc    240

tcgcctcctg cagccgcatc gcccgccgag ccacagccac gatgatcgcg ggctcccttc    300

tcctgcttgg attccttagc accaccacag ctcagccaga acagaaggcc tcgaatctca    360

ttggcacata ccgccatgtt gaccgtgcca ccggccaggt gctaacctgt gacaagtgtc    420

cagcaggaac ctatgtctct gagcattgta ccaacacaag cctgcgcgtc tgcagcagtt    480

gccctgtggg gacctttacc aggcatgaga atggcataga gaaatgccat gactgtagtc    540

agccatgccc atggccaatg attgagaaat taccttgtgc tgcc                      584
```

<210> SEQ ID NO 4
<211> LENGTH: 125
<212> TYPE: PRT
<213> ORGANISM: HOMO SAPIENS

<400> SEQUENCE: 4

```
Met Gly Thr Ser Pro Ser Ser Ser Thr Ala Leu Ala Ser Cys Ser Arg
1               5                   10                  15

Ile Ala Arg Arg Ala Thr Ala Thr Met Ile Ala Gly Ser Leu Leu Leu
            20                  25                  30

Leu Gly Phe Leu Ser Thr Thr Thr Ala Gln Pro Glu Gln Lys Ala Ser
        35                  40                  45

Asn Leu Ile Gly Thr Tyr Arg His Val Asp Arg Ala Thr Gly Gln Val
    50                  55                  60

Leu Thr Cys Asp Lys Cys Pro Ala Gly Thr Tyr Val Ser Glu His Cys
65                  70                  75                  80

Thr Asn Thr Ser Leu Arg Val Cys Ser Ser Cys Pro Val Gly Thr Phe
                85                  90                  95

Thr Arg His Glu Asn Gly Ile Glu Lys Cys His Asp Cys Ser Gln Pro
            100                 105                 110

Cys Pro Trp Pro Met Ile Glu Lys Leu Pro Cys Ala Ala
        115                 120                 125
```

<210> SEQ ID NO 5
<211> LENGTH: 588
<212> TYPE: DNA
<213> ORGANISM: HOMO SAPIENS
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature -continued

```
<222> LOCATION: (15)..(15)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t

<400> SEQUENCE: 5

gcgnccgcgn ngngngcaag gtgctgagcg cccctagngc ctcccttgcc gcctccctcc     60

tctgcccggc cgtagcagtg cacatggggt gttggaggta gatgggctcc cggccgggag    120

gcggcggtgg atgcggcgct gggcagaagc agccgccgat tccagctgcc ccgcgcgccc    180

cggccacctt gcgagtcccc ggttcagcca tggggacctc tccgagcagc agcaccgccc    240

tcggcctcct gcaaccgcat cgcccgccga gccacagcca cgatgatcgc gggctccctt    300

ctcctgcttg gattccttag caccaccaca gctcagccag aacagaaggc ctcgaatctc    360

attggcacat accgccatgt tgaccgtgcc accggccagg tgctaacctg tgacaagtgt    420

ccagcaggaa cctatgtctc tgagcattgt accaacacaa gcctgcgcgt ctgtcagcag    480

tgccctgtgg ggacctttac caggcatgag aatggcatag agaaatgcca tgactgtagt    540

cagccatgcc catggccaat gattgagaaa ttaccttgtg cctctgcc                588


<210> SEQ ID NO 6
<211> LENGTH: 102
<212> TYPE: PRT
<213> ORGANISM: HOMO SAPIENS

<400> SEQUENCE: 6

Met Ile Ala Gly Ser Leu Leu Leu Leu Gly Phe Leu Ser Thr Thr Thr
1               5                   10                  15

Ala Gln Pro Glu Gln Lys Ala Ser Asn Leu Ile Gly Thr Tyr Arg His
            20                  25                  30

Val Asp Arg Ala Thr Gly Gln Val Leu Thr Cys Asp Lys Cys Pro Ala
        35                  40                  45

Gly Thr Tyr Val Ser Glu His Cys Thr Asn Thr Ser Leu Arg Val Cys
    50                  55                  60

Gln Gln Cys Pro Val Gly Thr Phe Thr Arg His Glu Asn Gly Ile Glu
65                  70                  75                  80

Lys Cys His Asp Cys Ser Gln Pro Cys Pro Trp Pro Met Ile Glu Lys
                85                  90                  95

Leu Pro Cys Ala Ser Ala
            100
```

TUMOR NECROSIS RELATED RECEPTOR, TR7

This application is a divisional of U.S. application Ser. No. 09/314,844, filed May 19, 1999, now U.S. Pat. No. 6,660,839 which is a divisional of U.S. application of U.S. application Ser. No. 08/959,382, filed Oct. 28, 1997, now U.S. Pat. No. 6,013,476, which claims the benefit of U.S. Provisional Application No. 60/041,796, filed Apr. 2, 1997.

FIELD OF INVENTION

This invention relates to newly identified polynucleotides, polypeptides encoded by them and to the use of such polynucleotides and polypeptides, and to their production. More particularly, the polynucleotides and polypeptides of the present invention relate to Tumor necrosis factor receptor (TNF-R) family, hereinafter referred to as TR7. The invention also relates to inhibiting or activating the action of such polynucleotides and polypeptides.

BACKGROUND OF THE INVENTION

Many biological actions, such as responses to certain stimuli and natural biological processes, are controlled by factors such as cytokines. Cytokines generally act through receptors by engaging the receptor and producing an intracellular response.

For example, tumor necrosis factors (TNF) alpha and beta are cytokines which act through TNF receptors to regulate numerous biological processes, including protection against infection and induction of shock and inflammatory disease. The TNF molecules belong to the "TNF-ligand" superfamily, and act together with their receptors or counterligands, the "TNF-receptor" superfamily. So far, nine members of the TNF-ligand superfamily have been identified and ten members of the TNF-receptor superfamily have been characterized. Identified ligands include TNF-α, lymphotoxin-α (LT-α, also known as TNF-β), LT-β (found in complex heterotrimer LT-α2-β), FasL, CD40L, CD27L, CD30L, 4-1BBL, OX40L and nerve growth factor (NGF). The superfamily of TNF-receptors include the p55TNF receptor, p75TNF receptor, TNF receptor-related protein, FAS antigen or APO-1, CD40, CD27, CD30, 4-1BB, OX40, low affinity p75 and NGF-receptor (Meager, A., Biologicals, 22:291–295 (1994)).

Many members of the TNF-ligand superfamily are expressed by activated T-cells, which implies that they are necessary for T-cell interactions with other cell types which underlie cell ontogeny and functions. Considerable insight into the essential functions of several members of the TNF receptor family has been gained from the identification and creation of mutants which abolish the expression of these proteins. For example, naturally occurring mutations in the FAS antigen and its ligand cause lymphoproliferative disease (Watanabe-Fukunaga, R., et al., Nature 356:314 (1992)), perhaps reflecting a failure of programmed cell death. Mutations of the CD40 ligand cause an X-linked immunodeficiency state characterized by high levels of immunoglubulin M and low levels of immunoglobulin G in plasma, indicating faulty T-cell-dependent B-cell activation (Allen, R. C. et al., Science 259:990 (1993)). Targeted mutations of the low affinity nerve growth factor receptor cause a disorder characterized by faulty sensory innovation of peripheral structures (Lee, K. F. et al, Cell 69:737 (1992)).

TNF and LT-α are capable of binding to two TNF receptors (the 55- and 75-kd TNF receptors). A large number of biological effects elicited by TNF and LT-α acting through their receptors include hemorrhagic necrosis of transplanted tumors, cytotoxicity, endotoxic shock, inflammation, immunoregulation, proliferation and antiviral responses, as well as protection against the deleterious effects of ionizing radiation. TNF and LT-α are involved in the pathogenesis of a wide range of diseases, including endotoxic shock, cerebral malaria, tumors, autoimmuine disease, AIDS and graft-versus-host rejection (Beutler, B. and Von Huffel, C., Science 264:667–668 (1994)). Mutations in the p55 Receptor cause increased susceptibility to microbial infection.

Moreover, an approximately 80 amino acid domain near the C-terminus of TNFR1 (P55) and Fas has been reported as the "death domain," which is responsible for transducing signals for programmed cell death (Tartaglia et al., Cell 74:845 (1993)).

The effects of TNF family ligands and TNF family receptors are varied and influence numerous functions, both normal and abnormal, in the biological processes of the mammalian system. There is a clear need, therefore, for identification and characterization of such receptors and ligands that influence biological activity, both normally and in disease states. In particular, there is a need to isolate and characterize novel members of the TNF receptor family.

This indicates that these receptors have an established, proven history as therapeutic targets. Clearly there is a need for identification and characterization of further receptors which can play a role in preventing, ameliorating or correcting dysfunctions or diseases, including, but not limited to, chronic and acute inflammation, arthritis, septicemia, autoimmune diseases (such as inflammatory bowel disease and psoriasis), transplant rejection, graft versus host disease, infection, stroke, ischemia, acute respiratory disease syndrome, restenosis, brain injury, AIDS, bone diseases, cancer (such as lymphoproliferative disorders), atherosclerosis, and Alzheimers disease.

SUMMARY OF THE INVENTION

In one aspect, the invention relates to TR7 polypeptides and recombinant materials and methods for their production. Another aspect of the invention relates to methods for using such TR7 polypeptides and polynucleotides. Such uses include the treatment of chronic and acute inflammation, arthritis, septicemia, autoimmune diseases (such as inflammatory bowel disease and psoriasis), transplant rejection, graft versus host disease, infection, stroke, ischemia, acute respiratory disease syndrome, restenosis, brain injury, AIDS, bone diseases, cancer (such as lymphoproliferative disorders), atherosclerosis, and Alzheimers disease, among others. In still another aspect, the invention relates to methods to identify agonists and antagonists using the materials provided by the invention, and treating conditions associated with TR7 imbalance with the identified compounds. Yet another aspect of the invention relates to diagnostic assays for detecting diseases associated with inappropriate TR7 activity or levels.

DESCRIPTION OF THE INVENTION

Definitions

The entire disclosures of U.S. patent application Ser. No. 09/314,844, filed May 19, 1999, U.S. patent application Ser. No. 08/959,382, filed Oct. 28, 1997, now U.S. Pat. No. 6,013,476, and U.S. Provisional Patent Application No. 60/041,796, filed Apr. 2, 1997 is expressly incorporated by reference herein.

The following definitions are provided to facilitate understanding of certain terms used frequently herein. "TR7"

refers, among others, to a polypeptide comprising the amino acid sequence set forth in SEQ ID NO:2, or an allelic variant thereof. "Receptor Activity" or "Biological Activity of the Receptor" refers to the metabolic or physiologic function of said TR7 including similar activities or improved activities or these activities with decreased undesirable side-effects. Also included are antigenic and immunogenic activities of said TR7.

"TR7 gene" refers to a polynucleotide comprising the nucleotide sequence set forth in SEQ ID NO:1 or allelic variants thereof and/or their complements.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated", but the same polynucleotide or polypeptide separated from the coexisting materials of its natural state is "isolated", as the term is employed herein. "Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymol* (1990) 182:626–646 and Rattan et al., "Protein Synthesis: Posttranslational Modifications and Aging", *Ann NY Acad Sci* (1992) 663:48–62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H., and Lipton, D., *SIAM J Applied Math* (1988)48:1073). Methods conmmonly employed to determine identity or similarity between two sequences include, but are not limited to, those disclosed in Guide to Huge Computers, Martin J. Bishop, ed., Academic Press, San Diego, 1994, and Carillo, H., and Lipton, D., *SIAM J Applied Math* (1988) 48:1073. Methods to determine identity and similarity are codified in computer programs. Preferred computer program methods to determine identity and similarity between two sequences include, but are not limited to, GCS program package (Devereux, J., et al., *Nucleic Acids Research* (1984) 12(1):387), BLASTP, BLASTN, FASTA (Atschul, S. F. et al., *J Molec Biol* (1990) 215:403).

As an illustration, by a polynucleotide having a nucleotide sequence having at least, for example, 95% "identity" to a reference nucleotide sequence of SEQ ID NO: 1is intended that the nucleotide sequence of the polynucleotide is identical to the reference sequence except that the polynucleotide sequence may include up to five point mutations per each 100 nucleotides of the reference nucleotide sequence of SEQ ID NO: 1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5 or 3 terminal positions of the reference nucleotide sequence or anywhere between those terminal positions, interspersed either individually among nucleotides in the reference sequence or in one or more contiguous groups within the reference sequence.

Similarly, by a polypeptide having an amino acid sequence having at least, for example, 95% "identity" to a reference amino acid sequence of SEQ ID NO:2 is intended that the amino acid sequence of the polypeptide is identical to the reference sequence except that the polypeptide sequence may include up to five amino acid alterations per each 100 amino acids of the reference amino acid of SEQ ID NO: 2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

Polypeptides of the Invention

In one aspect, the present invention relates to TR7 polypeptides (or TR7 proteins). The TR7 polypeptides include the polypeptides of SEQ ID NOS:2 and 4; as well as polypeptides comprising the amino acid sequence of SEQ ID NO:2; and polypeptides comprising the amino acid sequence which have at least 80% identity to that of SEQ ID NO:2 over its entire length, and still more preferably at least 90% identity, and even still more preferably at least 95% identity to SEQ ID NO: 2. Furthermore, those with at least 97–99% are highly preferred. Also included within TR7 polypeptides are polypeptides having the amino acid sequence which have at least 80% identity to the polypeptide having the amino acid sequence of SEQ ID NO: 2 over its entire length, and still more preferably at least 90% identity, and even still more preferably at least 95% identity to SEQ ID NO: 2. Furthermore, those with at least 97–99% are highly preferred. Preferably TR7 polypeptides exhibit at least one biological activity of the receptor.

The TR7 polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Fragments of the TR7 polypeptides are also included in the invention. A fragment is a polypeptide having an amino acid sequence that entirely is the same as part, but not all, of the amino acid sequence of the aforementioned TR7 polypeptides. As with TR7 polypeptides, fragments may be "free-standing", or comprised within a larger polypeptide of which they form a part or region, most preferably as a single continuous region. Representative examples of polypeptide fragments of the invention, include, for example, fragments from about amino acid number 1–20, 21–40, 41–60, 61–80, 81–100, and 101 to the end of TR7 polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of TR7 polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-foming regions, hydrophilic regions, hydrophobic regions, alpha amphipathic regions, beta amphipathic regions, flexible regions, surface-forming regions, substrate binding region, and high antigenic index regions. Other preferred fragments are biologically active fragments. Biologically active fragments are those that mediate receptor activity, including those with a similar activity or an improved activity, or with a decreased undesirable activity. Also included are those that are antigenic or immunogenic in an animal, especially in a human.

Preferably, all of these polypeptide fragments retain the biological activity of the receptor, including antigenic activity. Among the most preferred fragment is that having the amino acid sequence of SEQ ID NO: 4. Variants of the defined sequence and fragments also form part of the present invention. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, or 1–2 amino acids are substituted, deleted, or added in any combination.

The TR7 polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

Another aspect of the invention relates to TR7 polynucleotides. TR7 polynucleotides include isolated polynucleotides which encode the TR7 polypeptides and fragments, and polynucleotides closely related thereto. More specifically, TR7 polynucleotide of the invention include a polynucleotide comprising the nucleotide sequence contained in SEQ ID NO:1 encoding a TR7 polypeptide of SEQ ID NO: 2, and polynucleotides having the particular sequences of SEQ ID NOS:1 and 3. TR7 polynucleotides further include a polynucleotide comprising a nucleotide sequence that has at least 80% identity over its entire length to a nucleotide sequence encoding the TR7 polypeptide of SEQ ID NO:2, and a polynucleotide comprising a nucleotide sequence that is at least 80% identical to that of SEQ ID NO:1 over its entire length. In this rsuch asard, polynucleotides at least 90% identical are particularly preferred, and those with at least 95% are especially preferred. Furthermore, those with at least 97% are highly preferred and those with at least 98–99% are most highly preferred, with at least 99% being the most preferred. Also included under TR7 polynucleotides are a nucleotide sequence which has sufficient identity to a nucleotide sequence contained in SEQ ID NO:1 to hybridize under conditions useable for amplification or for use as a probe or marker. The invention also provides polynucleotides which are complementary to such TR7 polynucleotides.

TR7 of the invention is structurally related to other proteins of the Tumor necrosis factor receptor (TNF-R) family, as shown by the results of sequencing the cDNA encoding human TR7. The cDNA sequence of SEQ ID NO:1 contains an open reading frame (nucleotide number 7 to 1974) encoding a polypeptide of 655 amino acids of SEQ ID NO:2. The amino acid sequence of Table 1 (SEQ ID NO:2) has about 35% identity (using BLAST (from GCG) ) in 168 amino acid residues with human osteoprotegerin (OPG) protein (Simonet W S, et al., *Cell* 89: 309–319 (1997)). The nucleotide sequence of Table 1 (SEQ ID NO:1) has about 65% identity (using BESTFIT (from GCG) ) in 102 nucleotide residues with Human Herpvesvirus Entry Mediator (HVEM) (Montgomery, R. I. et al., Cell 87, 427 (1996)) and 57% identity (using BESTFIT (from GCG)) in 118 nucleotide residues with human Osteoprotegerin (OPG) Protein (Simonet W S, et al., *Cell* 89: 309–319 (1997)). Thus TR7 polypeptides and polynucleotides of the present invention are expected to have, inter alia, similar biological functions/properties to their homologous polypeptides and polynucleotides, and their utility is obvious to anyone skilled in the art.

TABLE 1[a]

| | | | | | |
|---|---|---|---|---|---|
| 1 | TCAGCCATGG | GGACCTCTCC | GAGCAGCAGC | ACCGCCCTCG | CCTCCTGCAG |
| 51 | CCGCATCGCC | CGCCGAGCCA | CAGCCACGAT | GATCGCGGGC | TCCCTTCTCC |
| 101 | TGCTTGGATT | CCTTAGCACC | ACCACAGCTC | AGCCAGAACA | GAAGGCCTCG |
| 151 | AATCTCATTG | GCACATACCG | CCATGTTGAC | CGTGCCACCG | GCCAGGTGCT |
| 201 | AACCTGTGAC | AAGTGTCCAG | CAGGAACCTA | TGTCTCTGAG | CATTGTACCA |
| 251 | ACACAAGCCT | GCGCGTCTGC | AGCAGTTGCC | CTGTGGGGAC | CTTTACCAGG |
| 301 | CATGAGAATG | GCATAGAGAA | ATGCCATGAC | TGTAGTCAGC | CATGCCCATG |
| 351 | GCCAATGATT | GAGAAATTAC | CTTGTGCTGC | CTTGACTGAC | CGAGAATGCA |
| 401 | CTTGCCCACC | TGGCATGTTC | CAGTCTAACG | CTACCTGTGC | CCCCCATACG |
| 451 | GTGTGTCCTG | TGGGTTGGGG | TGTGCGGAAG | AAAGGGACAG | AGACTGAGGA |
| 501 | TGTGCGGTGT | AAGCAGTGTG | CTCGGGGTAC | CTTCTCAGAT | GTGCCTTCTA |
| 551 | GTGTGATGAA | ATGCAAAGCA | TACACAGACT | GTCTGAGTCA | GAACCTGGTG |
| 601 | GTGATCAAGC | CGGGGACCAA | GGAGACAGAC | AACGTCTGTG | GCACACTCCC |
| 651 | GTCCTTCTCC | AGCTCCACCT | CACCTTCCCC | TGGCACAGCC | ATCTTTCCAC |
| 701 | GCCCTGAGCA | CATGGAAACC | CATGAAGTCC | CTTCCTCCAC | TTATGTTCCC |
| 751 | AAAGGCATGA | ACTCAACAGA | ATCCAACTCT | TCTGCCTCTG | TTAGACCAAA |
| 801 | GGTACTGAGT | AGCATCCAGG | AAGGGACAGT | CCCTGACAAC | ACAAGCTCAG |
| 851 | CAAGGGGGAA | GGAAGACGTG | AACAAGACCC | TCCCAAACCT | TCAGGTAGTC |
| 901 | AACCACCAGC | AAGGCCCCCA | CCACAGACAC | ATCCTGAAGC | TGCTGCCGTC |
| 951 | CATGGAGGCC | ACTGGGGGCG | AGAAGTCCAG | CACGCCCATC | AAGGGCCCCA |
| 1001 | AGAGGGGACA | TCCTAGACAG | AACCTACACA | AGCATTTTGA | CATCAATGAG |

TABLE 1[a]-continued

| | |
|---|---|
| 1051 | CATTTGCCCT GGATGATTGT GCTTTTCCTG CTGCTGGTGC TTGTGGTGAT |
| 1101 | TGTGGTGTGC AGTATCCGGA AAAGCTCGAG GACTCTGAAA AAGGGGCCCC |
| 1151 | GGCAGGATCC CAGTGCCATT GTGGAAAAGG CAGGGCTGAA GAAATCCATG |

[a]A nucleotide sequence of a human TR7. (SEQ ID NO: 1)

TABLE 2[b]

| | |
|---|---|
| 1 | MGTSPSSSTA LASCSRIARR ATATMIAGSL LLLGFLSTTT AQPEQKASNL |
| 51 | IGTYRHVDRA TGQVLTCDKC PAGTYVSEHC TNTSLRVCSS CPVGTFTRHE |
| 101 | NGIEKCHDCS QPCPWPMIEK LPCAALTDRE CTCPPGMFQS NATCAPHTVC |
| 151 | PVGWGVRKKG TETEDVRCKQ CARGTFSDVP SSVMKCKAYT DCLSQNLVVI |
| 201 | KPGTKETDNV CGTLPSFSSS TSPSPGTAIF PRPEHMETHE VFSSTYVPKG |
| 251 | MNSTESNSSA SVRPKVLSSI QEGTVPDNTS SARGKEDVNK TLPNLQVVNH |
| 301 | QQGPHHRHIL KLLPSMEATG GEKSSTPIKG PKRGHPRQNL HKHFDINEHL |
| 351 | PWMIVLFLLL VLVVIVVCSI RKSSRTLKKG PRQDPSAIVE KAGLKKSMTP |
| 401 | TQNREKWIYY CNGHGIDILK LVAAQVGSQW KDIYQFLCNA SEREVAAFSN |
| 451 | GYTADHERAY AALQHWTIRG PEASLAQLIS ALRQHRRNDV VEKIRGLMED |
| 501 | TTQLETDKLA LPMSPSPLSP SPIPSPNAKL ENSALLTVEP SPQDKNKGFF |
| 551 | VDESEPLLRC DSTSSGSSAL SRNGSFITKE KKDTVLRQVR LDPCDLQPIF |
| 601 | DDMLHFLNPE ELRVIEEIPQ AEDKLDRLFE IIGVKSQEAS QTLLDSVYSH |
| 651 | LPDLL* |

[b]An amino acid sequence of a human TR7. (SEQ ID NO: 2).

One polynucleotide of the present invention encoding TR7 may be obtained using standard cloning and screening, from a cDNA library derived from mRNA in cells of human brain, heart, lung, thymus, kidney, small intestine, prostate, monocytes and endothelial cells, using the expressed sequence tag (EST) analysis (Adams, M. D., et al. *Science* (1991) 252:1651–1656; Adams, M. D. et al., *Nature*, (1992) 355:632–634; Adams, M. D., et al., *Nature* (1995) 377 Supp: 3–174). Polynucleotides of the invention can also be obtained from natural sources such as genomic DNA libraries or can be synthesized using well known and commercially available techniques.

The nucleotide sequence encoding TR7 polypeptide of SEQ ID NO:2 may be identical to the polypeptide encoding sequence contained in Table 1 (nucleotide number 7 to 1974 of SEQ ID NO:1), or it may be a sequence, which as a result of the redundancy (degeneracy) of the genetic code, also encodes the polypeptide of SEQ ID NO:2.

When the polynucleotides of the invention are used for the recombinant production of TR7 polypeptide, the polynucleotide may include the coding sequence for the mature polypeptide or a fragment thereof, by itself; the coding sequence for the mature polypeptide or fragment in reading frame with other coding sequences, such as those encoding a leader or secretory sequence, a pre-, or pro- or prepro-protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et aL, *Proc Natl Acad Sci USA* (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Further preferred embodiments are polynucleotides encoding TR7 variants comprising the amino acid sequence of TR7 polypeptide of Table 2 (SEQ ID NO:2) in which several, 5–10, 1–5, 1–3, 1–2 or 1 amino acid residues are substituted, deleted or added, in any combination. Among the preferred polynucleotides of the present invention is contained in Table 3 (SEQ ID NO: 3) encoding the amino acid sequence of Table 4 (SEQ ID NO: 4).

TABLE 3[c]

| | |
|---|---|
| 1 | GCGNCCGCGN NGNGNGCAAG GTGCTGAGCG CCCCTAGNGC CTCCCTTGCC |
| 51 | GCCTCCCTCC TCTGCCCGGC CGTAGCAGTG CACATGGGGT GTTGGAGGTA |

TABLE 3[c]-continued

| | | | | | |
|---|---|---|---|---|---|
| 101 | GATGGGCTCC | CGGCCGGGAG | GCGGCGGTGG | ATGCGGCGCT | GGGCAGAAGC |
| 151 | AGCCGCCGAT | TCCAGCTGCC | CCGCGCGCCC | CGGCCACCTT | GCGAGTCCCC |
| 201 | GGTTCAGCCA | TGGGGACCTC | TCCGAGCAGC | AGCACCGCCC | TCGCCTCCTG |
| 251 | CAGCCGCATC | GCCCGCCGAG | CCACAGCCAC | GATGATCGCG | GGCTCCCTTC |
| 301 | TCCTGCTTGG | ATTCCTTAGC | ACCACCACAG | CTCAGCCAGA | ACAGAAGGCC |
| 351 | TCGAATCTCA | TTGGCACATA | CCGCCATGTT | GACCGTGCCA | CCGGCCAGGT |
| 401 | GCTAACCTGT | GACAAGTGTC | CAGCAGGAAC | CTATGTCTCT | GAGCATTGTA |
| 451 | CCAACACAAG | CCTGCGCGTC | TGCAGCAGTT | GCCCTGTGGG | GACCTTTACC |
| 501 | AGGCATGAGA | ATGGCATAGA | GAAATGCCAT | GACTGTAGTC | AGCCATGCCC |
| 551 | ATGGCCAATG | ATTGAGAAAT | TACCTTGTGC | TGCC | |

[c]A partial nucleotide sequence of a human TR7. (SEQ ID NO: 3).

TABLE 4[d]

| | | | | | |
|---|---|---|---|---|---|
| 1 | MGTSPSSSTA | LASCSRIARR | ATATMIAGSL | LLLGFLSTTT | AQPEQKASNL |
| 51 | IGTYRHVDRA | TGQVLTCDKC | PAGTYVSEHC | TNTSLRVCSS | CPVGTFTRHE |
| 101 | NGIEKCHDCS | QPCPWPMIEK | LPCAA | | |

[d]A partial amino acid sequence of a human TR7. (SEQ ID NO: 4).

TABLE 5

| Nucleotide and Amino Acid sequence of a TR7 fragment (SEQ ID NOS: 5 and 6, respectively.) | | |
|---|---|---|
| 1 | GCGNCCGCGNNGNGNGCAAGGTGCTGAGCGCCCCTAGNGCCTCCCTTGCCGCCTCCCTCC | 60 |
| 61 | TCTGCCCGGCCGTAGCAGTGCACATGGGGTGTTGGAGGTAGATGGGCTCCCGGCCGGGAG | 120 |
| 121 | GCGGCGGTGGATGCGGCGCTGGGCAGAAGCAGCCGCCGATTCCAGCTGCCCCGCGCGCCC | 180 |
| 181 | CGGCCACCTTGCGAGTCCCCGGTTCAGCCATGGGGACCTCTCCGAGCAGCAGCACCGCCC | 240 |
| 241 | TCGGCCTCCTGCAACCGCATCGCCCGCCGAGCCACAGCCACGATGATCGCGGGCTCCCTT | 300 |
| | MetIleAlaGlySerLeu | 6 |
| 301 | CTCCTGCTTGGATTCCTTAGCACCACCACAGCTCAGCCAGAACAGAAGGCCTCGAATCTC | 360 |
| 7 | LeuLeuLeuGlyPheLeuSerThrThrThrAlaGlnProGluGlnLysAlaSerAsnLeu | 26 |
| 361 | ATTGGCACATACCGCCATGTTGACCGTGCCACCGGCCAGGTGCTAACCTGTGACAAGTGT | 420 |
| 27 | IleGlyThrTyrArgHisValAspArgAlaThrGlyGlnValLeuThrCysAspLysCys | 46 |
| 421 | CCAGCAGGAACCTATGTCTCTGAGCATTGTACCAACACAAGCCTGCGCGTCTGTCAGCAG | 480 |
| 47 | ProAlaGlyThrTyrValSerGluHisCysThrAsnThrSerLeuArgValCysGlnGln | 66 |
| 481 | TGCCCTGTGGGGACCTTTACCAGGCATGAGAATGGCATAGAGAAATGCCATGACTGTAGT | 540 |
| 67 | CysProValGlyThrpheThrArgHisGluAsnGlyIleGluLysCysHisAspCysSer | 86 |
| 541 | CAGCCATGCCATGGCCAATGATTGAGAAATTACCTTGTGCCTCTGCC | 588 |
| 87 | GlnProCysProTrpProMetIleGluLysLeuProCysAlaSerAla | 102 |

EXAMPLE 2

An EST (EST#1502886; Project ID: HHFGD57) with sequence similarity to the human TNF receptor was discovered in a commercial EST database. Analysis of the 588 nucleotide sequence of the partial cDNA, indicated that it encoded an open reading frame for a novel member of the TNF receptor superfamily and was named TR7. The predicted partial protein sequence is 102 amino acids long, with a hydrophobic amino-terminal leader sequence indicating that TR7 is expressed as a secreted or cell surface membrane bound protein. Comparison of the TR7 partial protein sequence with other TNF receptor family proteins indicates that it has at least one of the cysteine-rich repeats characteristic of the extracellular domains of this family.

The present invention further relates to polynucleotides that hybridize to the herein above-described sequences. In this regard, the present invention especially relates to polynucleotides which hybridize under stringent conditions to the herein above-described polynucleotides. As the term "stringent conditions" means hybridization will occur only if there is at least 80%, and preferably at least 90%, and more preferably at least 95%, yet even more preferably 97–99% identity between the sequences.

Polynucleotides of the invention, which are identical or sufficiently identical to a nucleotide sequence contained in SEQ ID NO:1 or a fragment thereof, may be used as hybridization probes for cDNA and genomic DNA, to isolate full-length cDNAs and genomic clones encoding TR7 and to isolate cDNA and genomic clones of other genes (including genes encoding homologs and orthologs from species other than human) that have a high sequence similarity to the TR7 gene. Such hybridization techniques are known to those of skill in the art. Typically these nucleotide sequences are 80% identical, preferably 90% identical, more preferably 95% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

In one embodiment, to obtain a polynucleotide encoding TR7 polypeptide, including homologs and orthologs from species other than human, comprises the steps of screening an appropriate library under stingent hybridization conditions with a labeled probe having the SEQ ID NO: 1 or a fragment thereof (including that of SEQ ID NO: 3), and isolating full-length cDNA and genomic clones containing said polynucleotide sequence. Such hybridization techniques are well known to those of skill in the art. Stringent hybridization conditions are as defined above or alternatively conditions under overnight incubation at 42° C. in a solution comprising: 50% formamide, 5×SSC (150 mM NaCl, 15 mM trisodium citrate), 50 mM sodium phosphate (pH7.6), 5× Denhardt's solution, 10% dextran sulfate, and 20 microgram/ml denatured, sheared salmon sperm DNA, followed by washing the filters in 0.1×SSC at about 65° C.

The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., *BASIC METHODS IN MOLECULAR BIOLOGY* (1986) and Sambrook et al., *MOLECULAR CLONING: A LABORATORY MANUAL*, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as *streptococci, staphylococci, E. coli, Streptomyces* and *Bacillus subtilis* cells; fungal cells, such as yeast cells and *Aspergillus* cells; insect cells such as *Drosophila* S2 and *Spodoptera* Sf9 cells; animal cells such as CHO, COS, HeLa, C127, 3T3, BHK, HEK 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., *MOLECULAR CLONING, A LABORATORY MANUAL* (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the TR7 polypeptide is to be expressed for use in screening assays, generally, it is preferred that the polypeptide be produced at the surface of the cell. In this event, the cells may be harvested prior to use in the screening assay. If TR7 polypeptide is secreted into the medium, the medium can be recovered in order to recover and purify the polypeptide; if produced intracellularly, the cells must first be lysed before the polypeptide is recovered.

TR7 polypeptides can be recovered and purified from recombinant cell cultures by wellknown methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of TR7 polynucleotides for use as diagnostic reagents. Detection of a mutated form of TR7 gene associated with a dysfunction will provide a diagnostic tool that can add to or define a diagnosis of a disease or susceptibility to a disease which results from under-expression, over-expression or altered expression of TR7. Individuals carrying mutations in the TR7 gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled TR7 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et al., *Science* (1985) 230:1242. Sequence changes at specific locations may also be revealed by nuclease protection assays, such as RNase and S1 protection or the chemical cleavage method. See Cotton et al, *Proc Natl Acad Sci USA* (1985) 85: 4397–4401. In another embodiment, an array of oligonucleotides probes comprising TR7 nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability. (See for example: M. Chee et al., Science, Vol 274, pp 610–613 (1996)).

The diagnostic assays offer a process for diagnosing or determining a susceptibility to chronic and acute inflammation, arthritis, septicemia, autoimmune diseases (such as inflammatory bowel disease and psoriasis), transplant rejection, graft versus host disease, infection, stroke, ischemia, acute respiratory disease syndrome, restenosis, brain injury, AIDS, bone diseases, cancer (such as lymphoproliferative disorders), atherosclerosis, and Alzheimers disease through detection of mutation in the TR7 gene by the methods described.

In addition, chronic and acute inflammation, arthritis, septicemia, autoimmune diseases (such as inflammatory bowel disease and psoriasis), transplant rejection, graft versus host disease, infection, stroke, ischemia, acute respiratory disease syndrome, restenosis, brain injury, AIDS, bone diseases, cancer (such as lymphoproliferative disorders), atherosclerosis, and Alzheimers disease, can be diagnosed by methods comprising determining from a sample derived from a subject an abnormally decreased or increased level of TR7 polypeptide or TR7 MRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as an TR7, in a sample derived from a host are well-known to those of skill in the art. Such assay methods include radioimmunoassays, competitive-binding assays, Western Blot analysis and ELISA assays.

Thus in another aspect, the present invention relates to a diagonostic kit for a disease or suspectability to a disease, particularly chronic and acute inflammation, arthritis, septicemia, autoimmune diseases (such as inflammatory bowel disease and psoriasis), transplant rejection, graft versus host disease, infection, stroke, ischemia, acute respiratory disease syndrome, restenosis, brain injury, AIDS, bone diseases, cancer (such as lymphoproliferative disorders), atherosclerosis, and Alzheimers disease, which comprises:

(a) a TR7 polynucleotide, preferably the nucleotide sequence of SEQ ID NO: 1, or a fragment thereof;
(b) a nucleotide sequence complementary to that of (a);
(c) a TR7 polypeptide, preferably the polypeptide of SEQ ID NO: 2, or a fragment thereof; or
(d) an antibody to a TR7 polypeptide, preferably to the polypeptide of SEQ ID NO: 2.

It will be appreciated that in any such kit, (a), (b), (c) or (d) may comprise a substantial component.

Chromosome Assays

The nucleotide sequences of the present invention are also valuable for chromosome identification. The sequence is specifically targeted to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

The differences in the cDNA or genomic sequence between affected and unaffected individuals can also be determined. If a mutation is observed in some or all of the affected individuals but not in any normal individuals, then the mutation is likely to be the causative agent of the disease.

Antibodies

The polypeptides of the invention or their fragments or analogs thereof, or cells expressing them can also be used as immunogens to produce antibodies immunospecific for the TR7 polypeptides. The term "immunospecific" means that the antibodies have substantiall greater affinity for the polypeptides of the invention than their affinity for other related polypeptides in the prior art.

Antibodies generated against the TR7 polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., *Nature* (1975) 256:495–497), the trioma technique, the human B-cell hybridoma technique (Kozbor et al., *Immunology Today* (1983) 4:72) and the EBV-hybridoma technique (Cole et al, MONOCLONAL ANTIBODIES AND CANCER THERAPY, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against TR7 polypeptides may also be employed to treat chronic and acute inflammation, arthritis, septicemia, autoimmune diseases (such as inflammatory bowel disease and psoriasis), transplant rejection, graft versus host disease, infection, stroke, ischemia, acute respiratory disease syndrome, restenosis, brain injury, AIDS, bone diseases, cancer (such as lymphoproliferative disorders), atherosclerosis, and Alzheimers disease, among others.

Vaccines

Another aspect of the invention relates to a method for inducing an immunological response in a mammal which comprises inoculating the mammal with TR7 polypeptide, or a fragment thereof, adequate to produce antibody and/or T cell immune response to protect said animal from chronic and acute inflammation, arthritis, septicemia, autoimmune diseases (such as inflammatory bowel disease and psoriasis), transplant rejection, graft versus host disease, infection, stroke, ischemia, acute respiratory disease syndrome, restenosis, brain injury, AIDS, bone diseases, cancer (such as lymphoproliferative disorders), atherosclerosis, and Alzheimers disease, among others. Yet another aspect of the invention relates to a method of inducing immunological response in a mammal which comprises, delivering TR7 polypeptide via a vector directing expression of TR7 polynucleotide in vivo in order to induce such an immunological response to produce antibody to protect said animal from diseases.

Further aspect of the invention relates to an immunological/vaccine formulation (composition) which, when introduced into a mammalian host, induces an immunological response in that mammal to a TR7 polypeptide wherein the composition comprises a TR7 polypeptide or TR7 gene. The vaccine formulation may further comprise a suitable carrier. Since TR7 polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

The TR7 polypeptide of the present invention may be employed in a screening process for compounds which bind the receptor and which activate (agonists) or inhibit activation of (antagonists) the receptor polypeptide of the present invention. Thus, polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See Coligan et al., *Current Protocols in Immunology* 1(2): Chapter 5 (1991).

TR7 polypeptides are responsible for many biological functions, including many pathologies. Accordingly, it is desirous to find compounds and drugs which stimulate TR7 on the one hand and which can inhibit the function of TR7 on the other hand. In general, agonists are employed for therapeutic and prophylactic purposes for such conditions as chronic and acute inflammation, arthritis, septicemia, autoimmune diseases (such as inflammatory bowel disease and psoriasis), transplant rejection, graft versus host disease, infection, stroke, ischemia, acute respiratory disease syndrome, restenosis, brain injury, AIDS, bone diseases, cancer (such as lymphoproliferative disorders), atherosclerosis, and Alzheimers disease. Antagonists may be employed for a variety of therapeutic and prophylactic purposes for such conditions as chronic and acute inflammation, arthritis, septicemia, autoimmune diseases (such as inflammatory bowel disease and psoriasis), transplant rejection, graft versus host disease, infection, stroke, ischemia, acute respiratory disease syndrome, restenosis, brain injury, AIDS, bone diseases, cancer (such as lymphoproliferative disorders), atherosclerosis, and Alzheimers disease.

In general, such screening procedures involve producing appropriate cells which express the receptor polypeptide of the present invention on the surface thereof. Such cells include cells from mammals, yeast, *Drosophila* or *E. coli*. Cells expressing the receptor (or cell membrane containing the expressed receptor) are then contacted with a test compound to observe binding, or stimulation or inhibition of a functional response.

The assays may simply test binding of a candidate compound wherein adherence to the cells bearing the receptor is detected by means of a label directly or indirectly associated with the candidate compound or in an assay involving competition with a labeled competitor. Further, these assays may test whether the candidate compound results in a signal generated by activation of the receptor, using detection systems appropriate to the cells bearing the receptor at their surfaces. Inhibitors of activation are generally assayed in the presence of a known agonist and the effect on activation by the agonist by the presence of the candidate compound is observed.

Further, the assays may simply comprise the steps of mixing a candidate compound with a solution containing a TR7 polypeptide to form a mixture, measuring TR7 activity in the mixture, and comparing the TR7 activity of the mixture to a standard.

The TR7 cDNA, protein and antibodies to the protein may also be used to configure assays for detecting the effect of added compounds on the production of TR7 MRNA and protein in cells. For example, an ELISA may be constructed for measuring secreted or cell associated levels of TR7 protein using monoclonal and polyclonal antibodies by standard methods known in the art, and this can be used to discover agents which may inhibit or enhance the production of TR7 (also called antagonist or agonist, respectively) from suitably manipulated cells or tissues. Standard methods for conducting screening assays are well understood in the art.

Examples of potential TR7 antagonists include antibodies or, in some cases, oligonucleotides or proteins which are closely related to the ligand of the TR7, e.g., a fragment of the ligand, or small molecules which bind to the receptor but do not elicit a response, so that the activity of the receptor is prevented.

Thus in another aspect, the present invention relates to a screening kit for identifying agonists, antagonists, ligands, receptors, substrates, enzymes, etc. for TR7 polypeptides; or compounds which decrease or enhance the production of TR7 polypeptides, which comprises:

(a) a TR7 polypeptide, preferably that of SEQ ID NO:2;

(b) a recombinant cell expressing a TR7 polypeptide, preferably that of SEQ ID NO:2;

(c) a cell membrane expressing a TR7 polypeptide; preferably that of SEQ ID NO: 2; or (d) antibody to a TR7 polypeptide, preferably that of SEQ ID NO: 2.

It will be appreciated that in any such kit, (a), (b), (c) or (d) may comprise a substantial component.

Prophylactic and Therapeutic Methods

This invention provides methods of treating an abnormal conditions related to both an excess of and insufficient amounts of TR7 activity.

If the activity of TR7 is in excess, several approaches are available. One approach comprises administering to a subject an inhibitor compound (antagonist) as hereinabove described along with a pharmaceutically acceptable carrier in an amount effective to inhibit activation by blocking binding of ligands to the TR7, or by inhibiting a second signal, and thereby alleviating the abnormal condition.

In another approach, soluble forms of TR7 polypeptides still capable of binding the ligand in competition with endogenous TR7 may be administered. Typical embodiments of such competitors comprise fragments of the TR7 polypeptide.

In still another approach, expression of the gene encoding endogenous TR7 can be inhibited using expression blocking techniques. Known such techniques involve the use of antisense sequences, either internally generated or separately administered. See, for example, O'Connor, *J Neurochem* (1991) 56:560 in *Oligodeoxynucleotides as Antisense Inhibitors of Gene Expression*, CRC Press, Boca Raton, Fla. (1988). Alternatively, oligonucleotides which form triple helices with the gene can be supplied. See, for example, Lee et al., *Nucleic Acids Res* (1979) 6:3073; Cooney et al., *Science* (1988) 241:456; Dervan et al., *Science* (1991) 251:1360. These oligomers can be administered per se or the relevant oligomers can be expressed in vivo.

For treating abnormal conditions related to an under-expression of TR7 and its activity, several approaches are also available. One approach comprises administering to a subject a therapeutically effective amount of a compound which activates TR7, i.e., an agonist as described above, in combination with a pharmaceutically acceptable carrier, to thereby alleviate the abnormal condition. Alternatively, gene therapy may be employed to effect the endogenous production of TR7 by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, *Gene Therapy and other Molecular Genetic-based Therapeutic Approaches*, (and references cited therein) in Human Molecular Genetics, T Strachan and A P Read, BIOS Scientific Publishers Ltd (1996).

Formulation and Administration

Peptides, such as the soluble form of TR7 polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof. Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1–100 μg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

EXAMPLE 1

Three ESTs (EST#1502886, EST#843791 and EST#2051015) with sequence similarity to the human TNF receptor were discovered in a commercial EST database. Analysis of two (EST# 843791 and EST# 2051015) nucleotide sequences, revealed that each was a partial sequence of the complete coding sequence, overlapping, with 100% identity, 108 bp at the nucleotide level. Together, the two sequences encompassed the complete predicted coding sequence of 1,968 bp, and encoded an open reading frame for a novel member of the TNF receptor superfamily and named TR7. The predicted protein is 655 amino acids long with a hydrophobic membrane spanning region indicating that at least one form of TR7 is expressed as a membrane-bound protein. Comparison of TR7 protein sequence, with other TNF receptor family proteins indicates that it has four of the cysteinerich repeats which are characteristic of the extracellular domains of this family, and of an intracellular death domain.

All publications, including but not limited to patents and patent applications, cited in this specification are herein incorporated by reference as if each individual publication were specifically and individually indicated to be incorporated by reference herein as though fully set forth.

What is claimed is:

1. An isolated polynucleotide comprising a nucleotide sequence encoding the amino acid sequence set forth in SEQ ID NO:4.

2. The isolated polynucleotide of claim 1, wherein said polynucleotide consists of the nucleotide sequence encoding the amino acid sequence set forth in SEQ ID NO:4.

3. The isolated polynucleotide of claim 1, wherein the polynucleotide comprises the nucleotide sequence set forth in SEQ ID NO:3.

4. The isolated polynucleotide of claim 3,wherein the polynucleotide consists of the nucleotide sequence set forth in SEQ ID NO:3.

5. An isolated TR7 polynucleotide comprising a nucleotide sequence that encodes at least 20 contiguous amino acids of the amino acid sequence set forth in SEQ ID NO:4.

6. The isolated TR7 polynucleotide of claim 5, wherein the nucleotide sequence encodes at least one cysteine-rich motif characteristic of an extracellular domain of Tumor Necrosis Factor Receptors.

7. The isolated TR7 polynucleotide of claim 5, wherein the nucleotide sequence encodes at least one Cys-x-x-Cys amino acid motif.

8. The isolated TR7 polynucleotide of claim 5, wherein the at least 20 contiguous amino acids of the amino acid sequence of SEQ ID NO:4 are also present in SEQ ID NO:2.

9. The isolated TR7 polynucleotide of claim 5, wherein the at least 20 contiguous amino acids of the amino acid sequence of SEQ ID NO:4 are also present in SEQ ID NO:6.

10. An isolated polynucleotide comprising a nucleotide sequence encoding the amino acid sequence set forth in SEQ ID NO:6.

11. The isolated polynucleotide of claim 10, wherein the polynucleotide consists of the nucleotide sequence encoding the amino acid sequence set forth in SEQ ID NO:6.

12. The isolated polynucleotide of claim 10, wherein the polynucleotide comprises the nucleotide sequence set forth in SEQ ID NO:5.

13. The isolated polynucleotide of claim 12, wherein the polynucleotide consists of the nucleotide sequence set forth in SEQ ID NO:5.

14. An isolated TR7 polynucleotide comprising a nucleotide sequence that encodes at least 20 contiguous amino acids of the amino acid sequence set forth In SEQ ID NO:6.

15. The isolated TR7 polynucleotide of claim 14 wherein the nucleotide sequence encodes at least one cysteine-rich motif characteristic of an extracellular domain of Tumor Necrosis Factor Receptors.

16. The isolated TR7 polynucleotide of claim 14 wherein the nucleotide sequence encodes at least one Cys-x-x-Cys amino acid motif.

17. The isolated TR7 polynucleotide of claim 14 wherein the at least 20 contiguous amino acids of the amino acid sequence of SEQ ID NO:6 are also present In SEQ ID NO:2.

* * * * *